United States Patent
Curtin et al.

(10) Patent No.: US 11,705,245 B2
(45) Date of Patent: Jul. 18, 2023

(54) SYSTEM AND METHODS FOR MAMMALIAN TRANSFER LEARNING

(71) Applicant: AI:ON Innovations, Inc., Mason, OH (US)

(72) Inventors: Sean Thomas Curtin, Mason, OH (US); Curtis Mitchel Stewart, Mason, OH (US); Ryan Matthew Gilbride, Cleveland, OH (US); Douglas Kirkpatrick, East Lansing, MI (US); Christopher Iovino, Miami, FL (US)

(73) Assignee: AI:ON Innovations, Inc., Mason, OH (US)

( * ) Notice: Subject to any disclaimer, the term of this patent is extended or adjusted under 35 U.S.C. 154(b) by 297 days.

(21) Appl. No.: 17/197,379

(22) Filed: Mar. 10, 2021

(65) Prior Publication Data
US 2021/0287045 A1 Sep. 16, 2021

Related U.S. Application Data

(60) Provisional application No. 62/987,441, filed on Mar. 10, 2020.

(51) Int. Cl.
*G16H 40/67* (2018.01)
*G06N 3/08* (2023.01)
(Continued)

(52) U.S. Cl.
CPC ......... *G16H 40/67* (2018.01); *G06F 18/2148* (2023.01); *G06N 3/08* (2013.01);
(Continued)

(58) Field of Classification Search
CPC ........ G16H 40/67; G16H 30/20; G06V 10/82; G06V 10/764; G06F 18/2148; G06N 3/08
See application file for complete search history.

(56) References Cited

U.S. PATENT DOCUMENTS

2009/0317788 A1* 12/2009 Laine ................. G01N 33/5073
435/325
2013/0108131 A1  5/2013 Abramoff et al.
(Continued)

FOREIGN PATENT DOCUMENTS

WO   WO-2010124257 A2 * 10/2010 ......... A61K 49/0008

OTHER PUBLICATIONS

International Search Report and Written Opinion of the International Searching Authority for International Patent App. No. PCT/US21/21770 dated Aug. 11, 2021 (10 pages).

*Primary Examiner* — Qun Shen
(74) *Attorney, Agent, or Firm* — Frost Brown Todd LLP; Vance V. VanDrake, III (57) ABSTRACT

A neural network is trained using transfer learning to analyze medical image data, including 2D, 3D, and 4D images and models. Where the target medical image data is associated with a species or problem class for which there is not sufficient labeled data available for training, the system may create enhanced training datasets by selecting labeled data from other species, and/or labeled data from different problem classes. During training and analysis, image data is chunked into portions that are small enough to obfuscate the species source, while being large enough to preserve meaningful context related to the problem class (e.g., the image portion is small enough that it can't be determined whether it is from a human or canine, but abnormal liver tissues are still identifiable). A trained checkpoint may then be used to provide automated analysis and heat mapping of input images via a cloud platform or other application.

19 Claims, 8 Drawing Sheets

(51) Int. Cl.
  *G16H 30/20*   (2018.01)
  *G06F 18/214*  (2023.01)
  *G06V 10/764*  (2022.01)
  *G06V 10/82*   (2022.01)

(52) U.S. Cl.
  CPC ............ *G06V 10/764* (2022.01); *G06V 10/82* (2022.01); *G16H 30/20* (2018.01)

(56) References Cited

U.S. PATENT DOCUMENTS

| | | | |
|---|---|---|---|
| 2013/0210666 A1* | 8/2013 | Jarvi | G01N 33/6893 506/18 |
| 2013/0259847 A1* | 10/2013 | Vishnudas | A61P 3/10 424/94.1 |
| 2013/0296183 A1* | 11/2013 | Eggan | A61P 43/00 506/9 |
| 2015/0072419 A1* | 3/2015 | Satomaa | C08B 37/00 435/372 |
| 2019/0197332 A1 | 6/2019 | Kavanau et al. | |
| 2020/0058126 A1 | 2/2020 | Wang et al. | |
| 2020/0285983 A1* | 9/2020 | Bhattacharyya | G06N 20/10 |
| 2020/0285997 A1* | 9/2020 | Bhattacharyya | G06N 7/00 |

\* cited by examiner

SYSTEM AND METHODS FOR MAMMALIAN TRANSFER LEARNING

PRIORITY

This application is a non-provisional filing of U.S. Provisional App. 62/987,441, filed Mar. 10, 2020, and titled "Systems and Methods of Mammalian Transfer Learning," the entire disclosure of which is hereby incorporated by reference herein.

BACKGROUND

Machine learning problems involving 3D image classification or segmentation often utilize large amounts of high-quality diverse labeled data to have a proper statistical sample of a problem space and allow for the creation of neural networks that are able to accurately perform a given task. This problem is exacerbated in portions of the medical imaging space, in both human and veterinary applications, due to the unique challenges of providing expert-labelled data for complex problems. Some data may be available in the properly labelled form for primarily human application (e.g., for radiology), while in other problems (e.g., histopathology) there exists a more comprehensive data set for animals (e.g., pigs in the case of histopathology). In order to broaden the applicability of machine learning techniques to human medical or veterinary applications where sufficient labelled data is lacking, there is a need for an improved system and method for transfer learning.

BRIEF DESCRIPTION OF THE DRAWINGS

The present disclosure will be more readily understood from a detailed description of some example embodiments taken in conjunction with the following figures.

DETAILED DESCRIPTION

Various non-limiting embodiments of the present disclosure will now be described to provide an overall understanding of the principles of the structure, function, and use of the systems and methods as disclosed herein. One or more examples of these non-limiting embodiments are illustrated in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment, or "in an embodiment" in places throughout the specification are not necessarily all referring to the same embodiment. Furthermore, the particular features, structures or characteristics may be combined in any suitable manner in one or more embodiments.

Throughout this disclosure, references to components or modules generally refer to items that logically can be grouped together to perform a function or group of related functions. Like reference numerals are generally intended to refer to the same or similar components. Components and modules can be implemented in software, hardware, or a combination of software and hardware. The term software is used expansively to include not only executable code, but also data structures, data stores, and computing instructions in any electronic format, firmware, and embedded software. The terms information and data are used expansively and can include a wide variety of electronic information, including but not limited to machine-executable or machine-interpretable instructions; content such as text, video data, and audio data, among others; and various codes or flags. The terms information, data, and content are sometimes used interchangeably when permitted by context.

The examples discussed herein are examples only and are provided to assist in the explanation of the systems and methods described herein. None of the features or components shown in the drawings or discussed below should be taken as mandatory for any specific implementation of any of these systems and methods unless specifically designated as mandatory. For ease of reading and clarity, certain components, modules, or methods may be described solely in connection with a specific figure. Any failure to specifically describe a combination or sub-combination of components should not be understood as an indication that any combination or sub-combination is not possible. Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As has been described, there is a need for a system and method for mammalian transfer learning that combines different datasets, where some amount of data comes from a different animal or problem, to allow for the training of neural networks capable of performing tasks with a high degree of accuracy. The availability of comprehensively labelled, task-specific data sets is conventionally required for the ability to train artificial intelligences (e.g., artificial neural networks) to recognize and detect specified features within those datasets or new instances of the same type of data (e.g. display the difference between healthy tissue and cancerous or abnormal growths within an MRI scan of a biological body). Multiple factors are assessed in producing a 'high quality' training input such that the AI trained using said input can output a solution to highlight abnormalities along with the specificity and accuracy of the AI's assessment of a desired abnormality specified by the positional label within the medical scan. The benefit of the AI is in the ability to dynamically both detect abnormalities below the range of a human interpreter's perception and without the limiting factors common to humans such as fatigue, oversaturated retinae, or an insufficient knowledge of cases that the human has not encountered, while also operating at a faster rate than humans. However, in conventional approaches, the tradeoff for this improved performance when using AI is a requirement of large quantities of data to efficiently train AI systems. The magnitude of the required datasets is generally on the order of tens or hundreds of thousands of data points, if not extending into in the millions.

Labelled data can refer to data which is additive to the primary image or information (e.g. CT scan, MRI, X-Ray, ultrasound, fMRI, multi-modality 2D, multi-modality 3D, multi-modality 4D) and stored in a separate file from the primary information. Labelled data can be stored in a digital file format such as, but not limited to .dicom, .dcm, .nii, .nifti, .mhd, .h, .jpg, .mpeg or any combination herein of either multi-dimensional data, including but not limited to 3D or 2D data. The labels may have a correspondence to the primary data's format and spatial orientation with the values contained within the labels' pixel/voxel. The label format may undergo a conversion of file type wherein the data is redefined from the original value-type to either another value-type or a voxel defined class. (e.g., class 0=background, class 1=organ, class 2=cancer). The voxel defined class values are not limited to a set number of units or classification types in the label file and can be dynamically assigned, sorted and disseminated into any multitude of data classifications designated by the user. As one example, labels may be a set of metadata that corresponds to a set of image data, with such correspondence being expressed as a per-pixel or per-voxel association of some characteristic that is not expressly present in the image data.

Labeled data can be sourced from multiple machines, methods and subjects. Label traits may include but are not limited to the species, the type of label, and label class options or values. Each piece of data is sourced from a single subject species. The label types may include but are not limited to classification, bounding box regression, and segmentation. Classification label values are a categorical value; bounding boxes regression label values are coordinate centers and box dimensions that denote the location of an object in the input data; and segmentation is, for example, either a binary heatmap or a heatmap with a categorical class values for each voxel. Labeled input within the scope of this art will focus on the subject of the data which will be referred to as 'human', 'animal', and 'alternate animal' where alternate animal refers to another animal species differing than the previous to input into the training data (e.g. canine, porcine, equine, feline, and rodent) and 'species' can refer to any single animal in the mammalian set. The label class options and values may include but are not limited to specific tissues, organs, organelles, and abnormalities.

Comprehensive labeled human medical data sets (including but not limited to modalities such as CT, MRI, X-Ray, ultrasound, and histopathology) are available in greater quantity than labeled animal-based veterinary data of similar modality as there is a relative scarcity of labelled animal data. The relative scarcity of sufficiently labeled data also exists when translating from an abundance of animal sourced data to human sourced data, depending on the problem or modality considered. For example, there exists quantitatively more labeled histopathology data for animal subjects (primarily pigs) than for humans. To address the discrepancy of volume in high quality labeled data within the medical and veterinarian image analysis problem space, in accordance with the present disclosure, labeled data from a specific species can be used to train the AI to detect abnormalities fully or partially supplemented from an alternative species (e.g., adding labelled human data to help detect canine abnormalities). To facilitate this supplementation, the modalities and categorical labels may be preserved throughout all selected sets in all sessions of training, validation, and testing.

Figure 1:
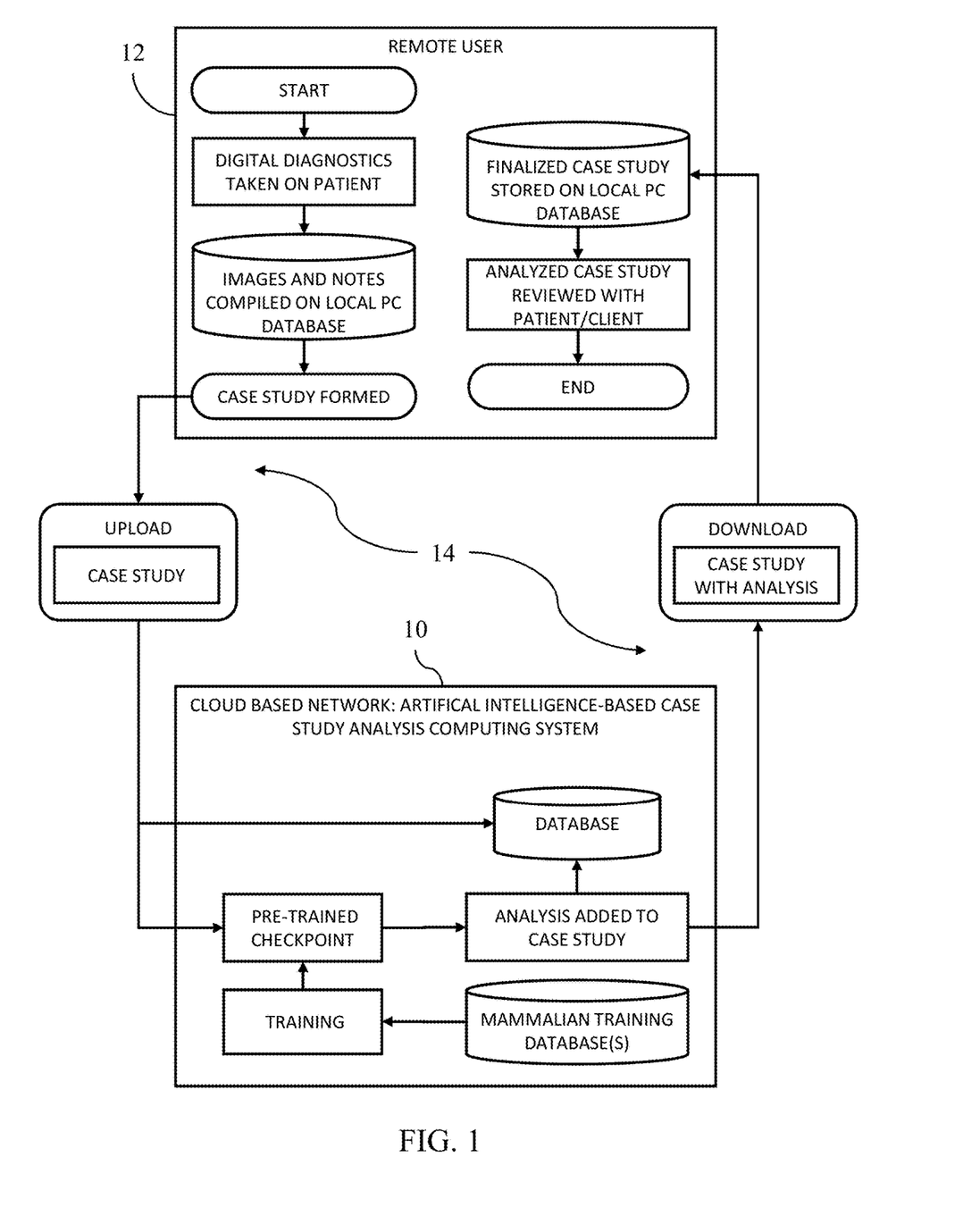
FIG. 1 shows a schematic diagram of an exemplary system configured for mammalian transfer learning.

Some implementations of the disclosed technology may include a cloud-based platform which can be accessed by, for example, medical professionals, patients, insurance companies, or other parties seeking analysis of radiology scans. FIG. 1 schematically illustrates an artificial intelligence-based case study analysis computing system (10) that can be accessed by a user device (12) over a network (14) (e.g., a LAN, WAN, or other communication network), though it should be understood that the disclosed technology may also be implemented as a standalone, locally executed software application. The computing system (10) may include one or more servers (e.g., physical servers, virtual servers, cloud servers, or other computing environments), and each server may include processors, memories, storage devices, communication devices, graphical processors, and other components as commonly used in the transfer, manipulation, and analysis of data. The user device (12) may be, for example, a computer, laptop, smartphone, tablet, hospital information system, medical imaging device (e.g., Mill machine or other digital imager), or other device capable of communicating with the computing system (10).

The artificial intelligence-based case study analysis computing system can be trained on labeled mammalian data, such as human-only data or a combination of human and animal data. In such an example, the remote user (12) may be, for example, an information system of a veterinarian seeking analysis of scans of an animal organ to aid in diagnosis.

As is illustrated, the remote user (12) can begin the process with a patient exam and collection of digital diagnostic, such as one or more scans of organ or organs. The user can form a case study for the animal under examination and upload the case study to the artificial intelligence-based case study analysis computing system. While the content of the uploaded case study may vary, the case study can comprise one or more scans of a particular organ or organs of an animal, as collected by the veterinarian's imaging equipment. Such upload can occur through any suitable data transmission technique, such as through an online web-based portal, software application interface, or other communication channel, for example.

Upon receipt of the case study from the remote user, the artificial intelligence-based case study analysis computing system can perform case study analysis based on its imaging models and add the analysis to the case study. The analysis of the processing can be added to the case study using any of a suitable number of approaches. In one embodiment, for example, the artificial intelligence-based case study analysis computing system augments the case study with a color-coded heat map to visually indicate potentially problematic areas. The case study with the analysis can then be downloaded, or otherwise transmitted or provided, to the remote user. The remote user can take appropriate next steps based on the analysis of the case study provided by the artificial intelligence-based case study analysis computing system.

In accordance with various embodiments, the systems and methods can be provided as a software platform or application that analyzes past case studies to form reference points for anomalous findings and can report on those findings. Thus, a more diagnostically complete visual analysis of the case can be provided without limiting the ultimate findings to particular diseases that are visually present within predefined, specific parameters.

Figure 2:
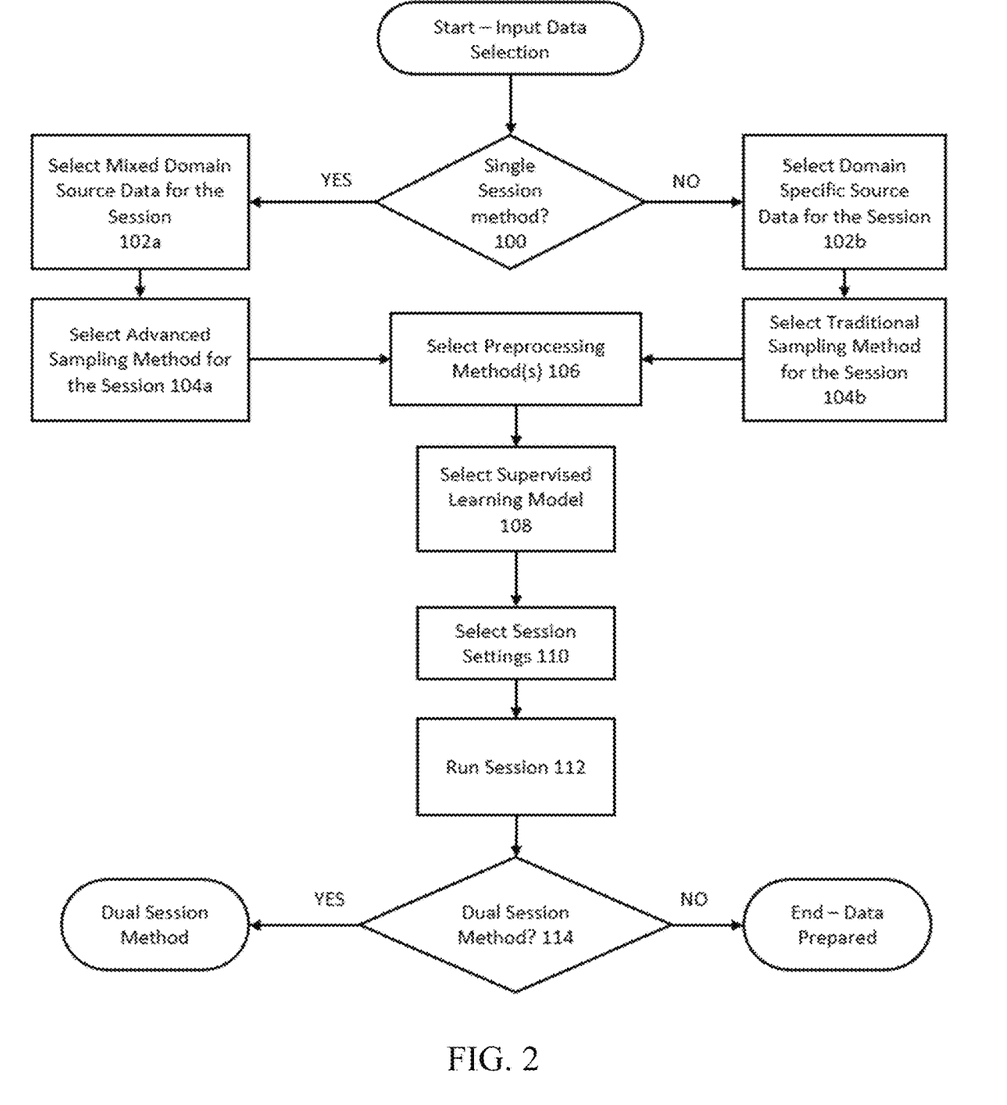
FIG. 2 shows a flowchart of an exemplary set of steps that may be performed during a first session of a mammalian transfer learning process.

The labeled data enters the system through the process shown in FIG. 2, which schematically illustrates example process flows for both training, validation, and testing sessions for transfer learning in accordance with the present disclosure. As shown, process flows in accordance with the present disclosure can have varying levels of tuning and testing, as may depend on a desired level of accuracy sought, availability of resources, and/or other operational parameters. In accordance with various embodiments, the systems and methods described herein using one or more of the process flows depicted in FIGS. 2-3 as a non-limiting use case example can achieve confidence levels of at least 70% in some embodiments while other embodiments can achieve peak confidence levels which exceed 95%. In an additional non-limiting use case example, accuracy levels in cases of liver, lung, kidney, and spleen masses/tumors for 20-80 lb. cats and dogs can exceed 80%, while in other embodiments, accuracy levels can exceed 85% or 87%.

With reference to FIG. 2, single session method, (100), controls if the single session method is applied to the first learning session. The single session method allows the user to train using data outside of the species application list, where the species application list refers to the intended use case of the model in the field so long as the same class labels are used within the same instance. Single session method refers to a method of object detection and instance segmentation models that experience a type of configurable window or reorientation of values while sampling for region proposals. The model achieves the ability to stratify the labeled input data from multiple sources before applying the target data by dividing the labeled input data into 'chunks' defined as a sub-section of the original scan/information which are small enough to obfuscates the species of the data example while still being large enough for the model to classify internal organs, abnormalities, and other feature classes. These subsets will be referred to as 'chunks' throughout the remainder of the document.

In FIG. 2, the system may select mixed source data for the session (102*a*) where the method is configured for a single session (100). A mixed source data set means that data from more than one species and one or more classes is used to form a data set that can later be split into a training, validation, and testing set. The user should also specify a species application list that will later be used by the advanced sampling method. Mixed source data can be sourced from, but not limited to the following scenarios where 'alternate animal' data can refer to one or more animal species that is not in the same species as the first animal (e.g. animal=canine, alternate animal=feline and porcine): labeled human training data applied to animal testing data, labeled animal training data applied to animal testing data, labeled animal training data applied to alternate animal testing data, labeled animal training data applied to human testing data, a combination of labeled human and animal training data applied to animal testing data, a combination of labeled human and animal training data applied to human testing data, a combination of labeled human and animal training data applied to alternate animal testing data, a combination of labeled human, animal and alternate animal training data applied to animal testing data, a combination of labeled human, animal and alternate animal training data applied to human testing data or any combination of the preceding.

Figure 4:
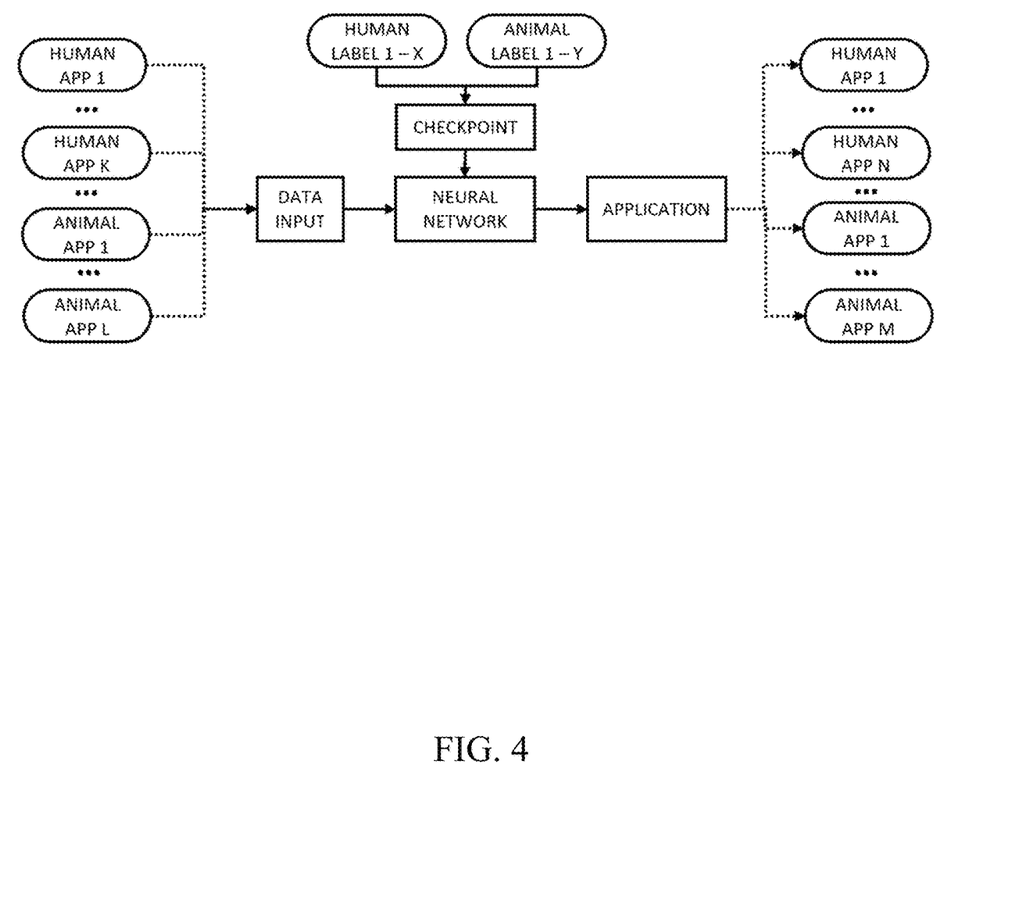
FIG. 4 shows a schematic diagram illustrating possible combinations of training data.

The distribution of source data and corresponding applications is demonstrated in FIG. 4, which illustrates how different data sources are collated and used together in the transfer learning process. That figure illustrates that different applications can be combined together to form a unified solution. Applications may be defined to be different formats of data that could be fed to the system, including but not limited to different data modalities (including but not limited to T1 or T2 scans in the MRI field), scan types (including but not limited to ultrasound, MRI, or CT scans), label or object types, or problems (including but not limited to different medical issues such as cancer or other medical anomalies) coming from human or veterinary solutions, where animal applications can consist of modalities or scans coming from different species of animals.

In FIG. 2, where the system is configured for more than a single session (100), select source specific data for the session (102*b*) is where the user selects a single species and one or more classes to form a data set that can later be split into a training, validation, and testing set. The species application matches the species selected by the user. Some examples for source data can be sourced from, but not limited to the following scenarios: labeled human training data applied to human testing data, labeled animal training data applied to animal testing data, labeled alternate animal training data applied to alternate animal testing.

With mixed domain data selected (102*a*), the system may select an advanced sampling method (104*a*) that may use stratified sampling methods to control what species are sampled for different data sets. The user should provide the parameters to control the sampling method. The configurations should be selected to allow any of the source data to be used for training while only allowing target data that matches the target application list to be used for testing and validation sets.

With domain specific data selected (102*b*), the system may select a traditional sampling method (104*b*) that may include but is not limited to simple random sampling and systematic sampling methods. in the case that systematic sampling is selected, the user should also provide the parameters to control the sampling method.

Figure 3:
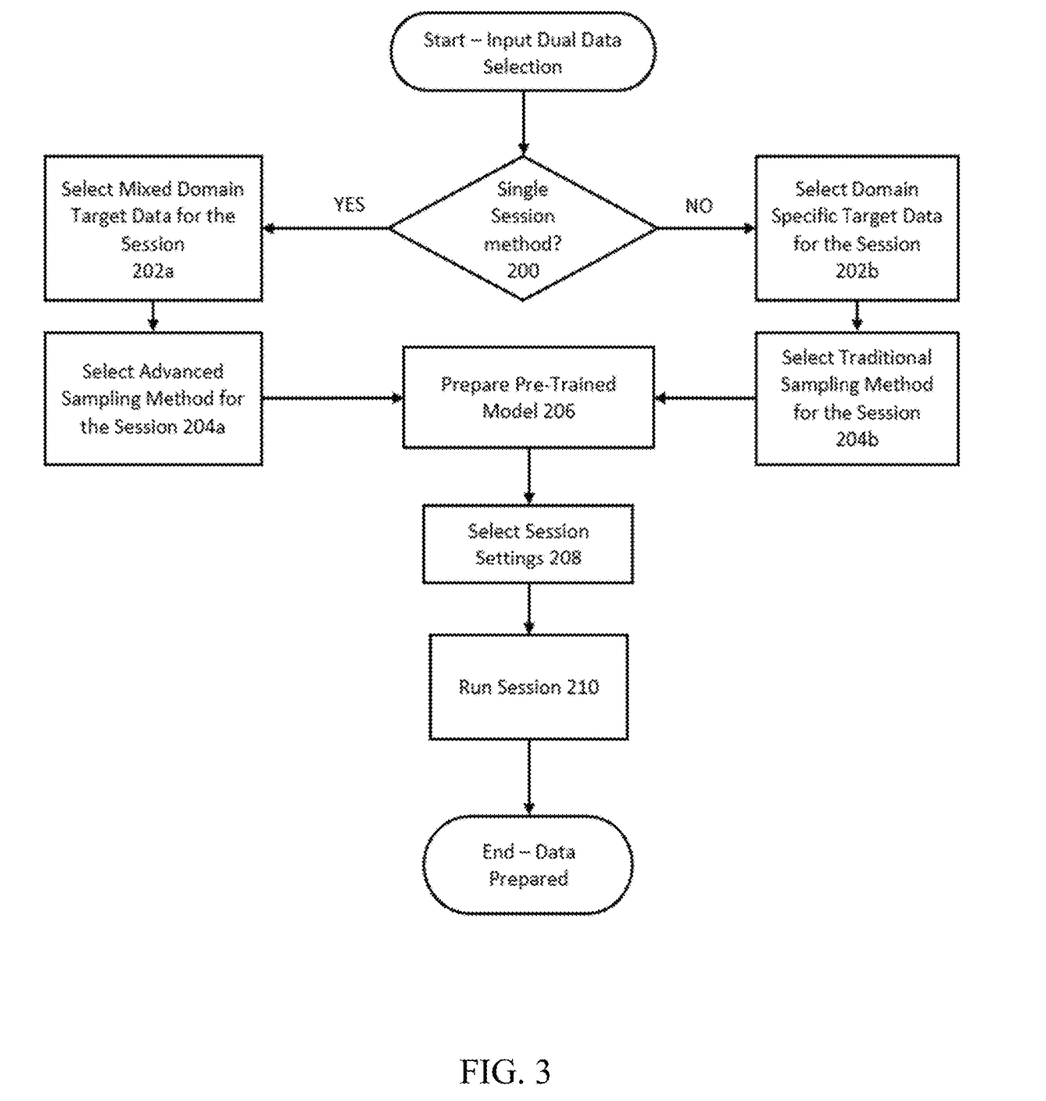
FIG. 3 shows a flowchart of an exemplary set of steps that may be performed during an optional second session of a mammalian transfer learning process.

The purpose of the preprocessing methods, shown in this disclosure in FIGS. 2 and 3, is to minimize the input image volume and or channels while maximizing the input features capacity. The preprocessing helps differentiate examples into their class label groups when processed with a trained learning model. In this manner, the system may select preprocessing methods (106), which may include but are not limited to feature normalization, image scaling, feature engineering, and a 2D to 4D custom version of the sliding window method that will be referred to as the sliding window method. The sliding window method is used for classification and semantic segmentation models, such as but not exclusive to, the u-net used to demonstrate the transfer learning methods described herein, to simulate the impact of a region proposal method or similar alternative. This reframing into a part versus whole window method causes the data between different species to grow increasingly similar. The smaller the data subset, window or 'chunks', the greater the similarity between the labeled input data and target data. However, the windows are only useful if they are large enough for the model to correctly differentiate between the class labels using the window input image. Other preprocessing methods alter the scale of the images before the window is applied and the optimal window size changes as a result. The differing methodologies create different types of inputs, thereby affecting all processing of the information possible by the AI. A post process is necessary in the event that the sliding windows method is used on a model to reconstruct final outputs. In the case of a classification network, this would result in the outputs being condensed into a single output class vector.

Model selection involves picking a learning model to perform any version of transfer learning on. Transfer learning can be applied to all supervised learning models and model types for image processing. Model selection (108), is the process of picking one of these model types. Examples may include but are not limited to classification, semantic segmentation, object detection, and instance segmentation. Different model types may require data with values for different groups of label types. Classification model data examples need classification label types. Data examples for a semantic segmentation model need segmentation label types. Data examples for an object detection model need classification and bounding box regression label types. Data examples for an instance segmentation model need classification, bounding box regression, and segmentation label types. Examples of classification models include but are not limited to VGG, ResNet, SE-ResNet, SENet, DenseNet, Inception Net, mobile net, EfficientNet, and Alex Net. A sub network can be added to classify data with a temporal dimension. Examples include but are not limited to an RNN, LSTM, or GRU. Examples of semantic segmentation models include but are not limited to u-net, Linknet, PSPNet, and FPN. Examples of object detection models include but are not limited to r-cnn, fast r-cnn, faster r-cnn, RetinaNet, and YOLO. Examples of instance segmentation models include but are not limited to YOLACAT, mask r-cnn, DETR. Object detection and instance segmentation model types break images up into smaller regions before computing the class, bounding box update, and or segmentation mask. When diagnostic images of humans and other mammalian species are diced into smaller images, it is hard to distinguish which chunk came from which species. The same phenomenon can result from a classification or semantic segmentation model if the sliding windows algorithm is implemented in the pre-processing selection. The implementations of the disclosed model that will be addressed in the context of this document is a u-net performing semantic segmentation using a custom implementation of a sliding window in the preprocessor.

The user selection of settings (110), as shown in FIG. 2 may include, but are not limited to, the data split ratios (for the training set, validation set, and testing set, sampled from the selected domains and classes), a loss function, an optimizer, a learning method, a Batch Size if applicable, and a number of Epochs. The settings can also optionally include data augmentation method(s), metric(s), and hyper parameters. Although these settings are not directly related to the unique applications and methods of transfer learning described herein, the selection of these settings is related to any model's effectiveness to fit the data, and such selections will be apparent to those of ordinary skill in the art in light of this disclosure.

With regards to the data split ratios in the settings, another point of distinction would be the fact that a larger portion of data is utilized for this application as testing/validation relative to the training dataset size. This includes the number of supplemental data cases selected relative to the target case that is being solved for. For example, where the target case is liver cancer in felines, the supplemental data cases selected for training include but are not limited to liver cancer in humans, liver cancer in canines, and adrenal mass cancer in humans. Non-limiting examples of ratios for target cases to supplemental cases include 2 other cases to 1 target case, 3 other cases to 1 target case, 4 other cases to 1 target case, 5 other cases to 1 target case, 6 other cases to 1 target case, 7 other cases to 1 target case, 8 other cases to 1 target case, 9 other cases to 1 target case, 10 other cases to 1 target case, 11 other cases to 1 target case, 12 other cases to 1 target case, 13 other cases to 1 target case, 14 other cases to 1 target case, 15 other cases to 1 target case, 16 other cases to 1 target case, 17 other cases to 1 target case, 18 other cases to 1 target case, 19 other cases to 1 target case, 20 other cases to 1 target case.

Examples of data augmentation methods may include but are not limited to random reorientation of slices with respect to one of the x, y, or z axes; blur of some intensity applied to a slice; or manipulation of the scale of one of the x, y, or z axes. Data augmentation methods, as applied in the typical use of the art, are only applied to the training data sets of a session.

The metric setting examples include but are not limited to the f1 score, precision, recall, specificity, accuracy, DICE coefficient, and other confusion matrix metrics, as well as their Multi-Class Confusion Matrix equivalents.

Loss function setting examples include but are not limited to Mean Square Error, Mean Absolute Error, Hinge Loss, and Cross Entropy Loss.

The optimizer may use the training data to generate iterative updates to the model with the goal of reducing the error score generated by the loss function. Examples of optimizers include but are not limited to Momentum, Nesterov accelerated gradient, Adagrad, Adadelta, RMSprop, Adam, AdaMax, Nadam, and AMSGrad.

Learning methods control how much of the data set is considered for calculating the model update. Examples of learning methods include but are not limited to Stochastic Gradient Descent, Batch Gradient Descent, and Mini-batch Gradient Descent.

In the event that the user has selected Batch Gradient Descent or Mini-batch Gradient Descent for the learning method in the settings, the user would then need to supply a batch size. Examples of batch sizes may include but are not limited to 1, 2, 5, 10, 12, 15, 20, 24, 30, 32, 36, 40, 42, 45, 50, 52, 60, 64, 70, 72, 80, 82, 84, 90, 96, and 100.

Epochs refer to the number of times the session iterates through the training and validation data sets. Implementations of the disclosed system are able to arrive at a meaningful solution by training the neural networks using a varying number of epochs; varying implementations include but are not limited to about 3 epochs, about 5 epochs, about 7 epochs, about 10 epochs, about 15 epochs, about 20 epochs, about 25 epochs, about 30 epochs, about 35 epochs, about 40 epochs, about 45 epochs, about 50 epochs, about 60 epochs, about 70 epochs, about 80 epochs, about 90 epochs, about 100 epochs, about 150 epochs, about 200 epochs, about 250 epochs, about 300 epochs, about 350 epochs, about 400 epochs, about 450 epochs, about 500 epochs, about 550 epochs, about 600 epochs, about 650 epochs, about 700 epochs, about 750 epochs, about 800 epochs, about 850 epochs, about 900 epochs, about 950 epochs, about 1,000 epochs. Other methods allow for the number of epochs to be determined during a session by setting conditions for how the metric histogram scores of training and validation compare.

Hyperparameters control how a model or its settings can be modified, iteratively, to search for a better model for the problem during validation. Examples may include but are not limited to any of the following: alternative settings, model properties like the activation functions used, the number of layers deep and wide, the layer kernels and kernel sizes, learning rate, dropout, regularization, and auxiliary output layers.

In FIG. 2, run session (112) uses the selected data, model, and settings to execute the Training, Validation, and Testing session. This should produce histogram values for the loss function and metrics for both the training and validation steps as well as error and metric scores for the test step. The training and validation cycle will update the model for the number of epochs specified in some embodiments or in other embodiments until a user specified goal for the loss and metrics for training and validation histograms have been met.

The dual session decision block is where the user can choose to end the process flow after the first session, at their own discretion or continue to the second session (114). Where the session is a single session method (114), the process ends and the application is trained and ready for use to analyze case studies from actual patients. Where the session is a dual session method (114), the system may proceed to the steps of FIG. 3. The single session decision block (200) in FIG. 3 is where the user can choose to use the dual session method on its own, or in conjunction with the single session method from FIG. 2 for the second session, regardless of whether or not the single session method was used previously in the first session.

For the dual session method shown in FIG. 3, the system may select mixed target data for the session (202a) indicating that the first session method is being used for the second session. A mixed target data set means that data from more than one species and one or more classes is used to form a data set that can later be split into a training, validation, and testing set. The user should also specify a species application list that will later be used by the or more classes to form a data set that can later be split into a training, validation, and testing set. Mixed target data can be sourced from, but not limited to the following scenarios: labeled human training data applied to animal testing data, labeled animal training data applied to animal testing data, labeled animal training data applied to alternate animal testing data, labeled animal training data applied to human testing data, a combination of labeled human and animal training data applied to animal testing data, a combination of labeled human and animal training data applied to human testing data, a combination of labeled human and animal training data applied to alternate animal testing data, a combination of labeled human, animal and alternate animal training data applied to animal testing data, a combination of labeled human, animal and alternate animal training data applied to human testing data or any combination of the preceding for the first session.

For the dual session method shown in FIG. 3, the system may select target specific data for the session (202b), which may include where the user selects a single species and one or more classes to form a data set that can later be split into a training, validation, and testing set. Some examples for target data can be sourced from, but not limited to the following scenarios: labeled human training data applied to animal testing data, labeled animal training data applied to animal testing data, labeled animal training data applied to alternate animal testing data, labeled animal training data applied to human testing data, a combination of labeled human and animal training data applied to animal testing data, a combination of labeled human and animal training data applied to human testing data, a combination of labeled human and animal training data applied to alternate animal testing data, a combination of labeled human, animal and alternate animal training data applied to animal testing data, a combination of labeled human, animal and alternate animal training data applied to human testing data or any combination herein.

Where a mixed domain target data is selected (202a), a user may select an advanced sampling method (204a) which may include the user selecting two configurations of the stratified sampling method to control what species are sampled for different data sets. The configurations should allow any of the target data to be used for training while only allowing data that matches the target application list.

Where a domain specific target data is selected (202b), a user may select a traditional sampling method (204b) that may include but is not limited to simple random sampling and systematic sampling methods.

In either case, the system may prepare a pre-trained model (206) for the dual session mammalian transfer learning method involving two optional steps; selecting early model layers to freeze for the next learning session and selecting late model layers to replace with randomly initialized layers. Such selections can be performed manually, although this disclosure is not limited to only manual selection. Ordinarily, replacing the final layers of a model is required for traditional transfer learning, but since the output classes of the disclosed applications are preserved between sessions, generalizable results can be achieved without this step. In general, the more layers frozen in the model, the less target species data needed to fit the model to the problem space as a result of using the dual session method described herein. As with the single session method, the dual session method may require that the class categories stay constant while the species may vary.

The modify settings process (208) from FIG. 3 is the point at which the user can change the settings that were previously used in the first learning session to optimize the generalizable score or output from the previous session. The hyperparameter selections at this point are limited to changes that do not change the pre-trained model architecture or preprocessing methods, as such changes would render the resulting system either unable to run or with meaningless output.

In FIG. 3, the run session (210) uses the selected data, model, and settings to execute the Training Validation and Testing session. This process should produce histograms for the loss function and metrics for both the training and validation cycle and then an error and metric scores for the test step. The training and validation cycle will update the model using the loss function, optimizer and other mandatory settings for the number of epochs specified (or until a user specified goal for the loss and metrics for training and validation histograms) has been met.

Figure 5:
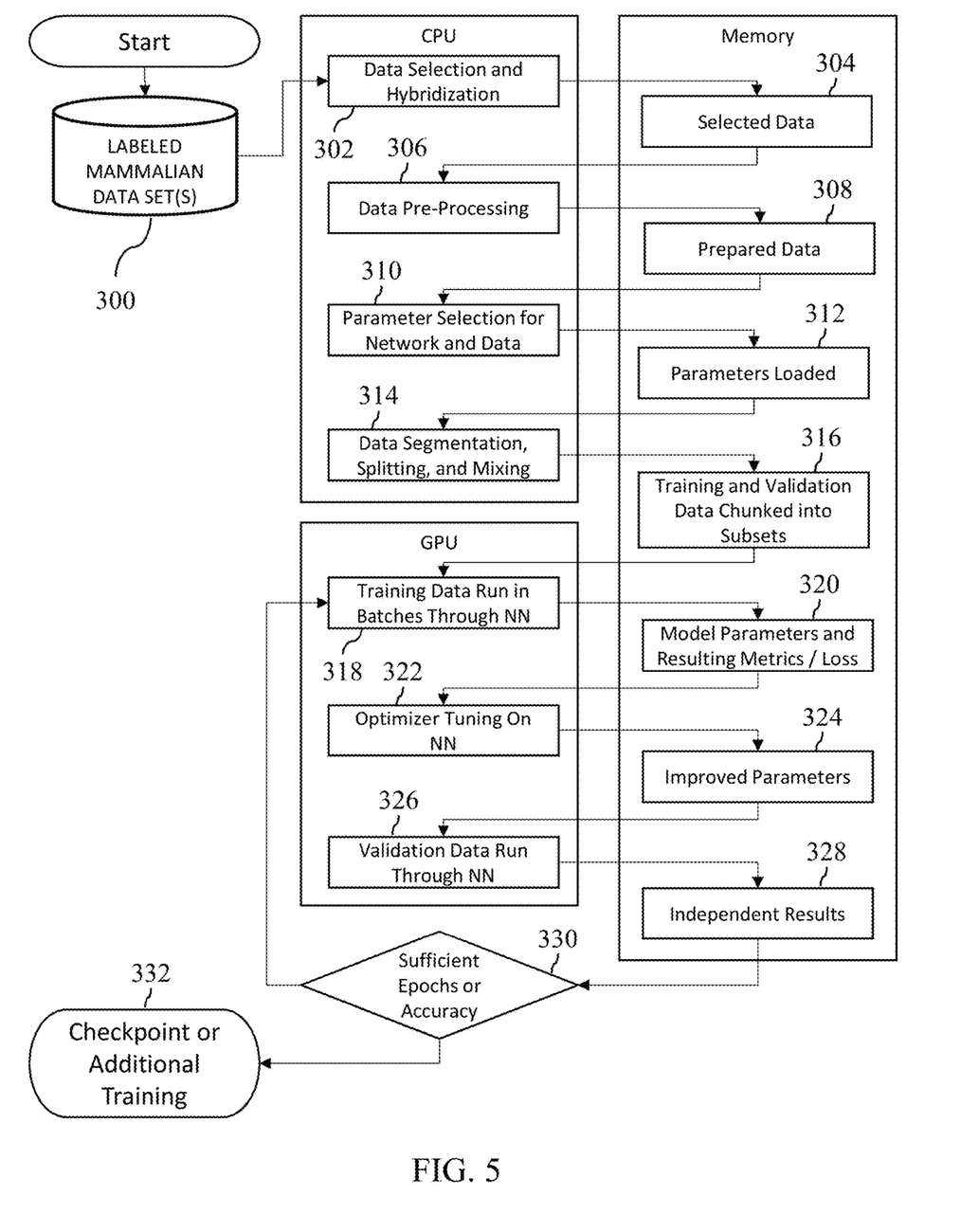
FIG. 5 shows a flowchart of an exemplary set of steps that may be performed during a training and validation process.

FIG. 5 shows a set of steps that may be performed during training and validation, such as may occur in relation FIGS. 2 and 3 (e.g., as part of a session that is run or executed (112, 210)). While FIGS. 5 and 6 show particular steps being performed by a "CPU" and "GPU", it should be understood that this is an example only, and that varying steps may be performed by either processing unit, or by a combination of CPUs, GPUs, TPUs, and other processing units.

The steps of FIG. 5 begin with providing and/or receiving one or more labeled mammalian data sets (300). The system selects (302) and hybridizes the one or more labeled mammalian datasets, and stores the selected data (304). The stored data is pre-processed (306) to convert it into a standardized format, and the prepared data is stored (308). Parameter selections are configured for the network and data (310), and the parameters are loaded (312) for use. The system then performs data segmentation, splitting, and mixing of the prepared data (314) in order to define segments, portions, or chunks of the prepared data, and these chunks are then stored (316). Defining these chunks may include creation of new files or datasets for each chunk, or may include the creation of metadata that may be applied to the prepared data in order to identify each chunk. The system then uses the data chunks to train the neural network (318) and save model parameters, resulting metrics, and loss characteristics (320). The system may utilize an optimizer to fine tune the performance of the neural network based upon the saved (320) characteristics, and may determine and save one or more improved parameters (324). The system may perform validation of the training (326) with the neural network in order to determine a set of independent results (328).

The system may then determine whether a sufficient number of epochs have been performed, and whether a sufficient level of accuracy has been reached (330) in the training of the neural network by comparing the independent results (328) to the standard results of the neural network with a similar input dataset. Where accuracy is insufficient, the system may proceed to a subsequent epoch by training the neural network (318) on the chunks with the improved parameters (324). Where accuracy is sufficient (330), the system may produce a checkpoint (332) of the neural network that is usable for testing and independent analysis of input datasets.

Figure 6:
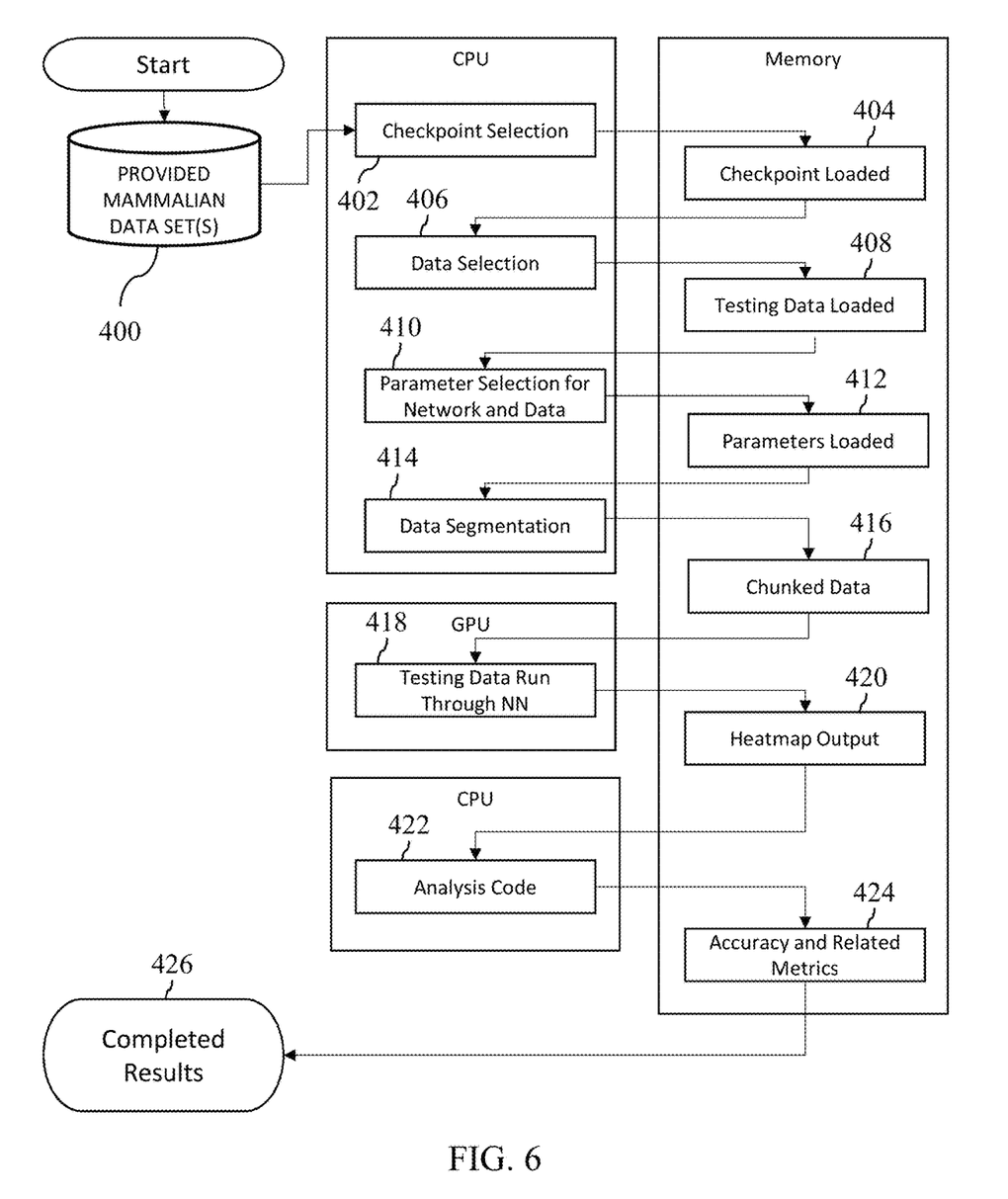
FIG. 6 shows a flowchart of an exemplary set of steps that may be performed during testing and application.

FIG. 6 shows a set of steps that may be performed during testing of a checkpoint version and during use of the neural network to analyze actual case studies. The system may access or receive (400) one or more mammalian datasets. These may be testing datasets usable to verify the effectiveness of the checkpoint version, or may be real world case studies received from users of the system. The system may select a checkpoint (402) for processing the data, and may access the checkpoint where it is stored (404). The system may perform data selection (406) to select cases that share some commonalities with the target data and load the testing data (408). Network and data parameters may be configured and/or selected (410), and those configurations may be loaded (412) to the neural network. The system may then perform data segmentation (414) to chunk the target case and related cases (416) into subsets. As with prior examples, this may include creating new datasets for chunks, or creating a set of metadata that defines the chunks within their original dataset. The system may then apply (418) the checkpoint neural network to the input cases and create a heatmap output (420).

Figure 7:
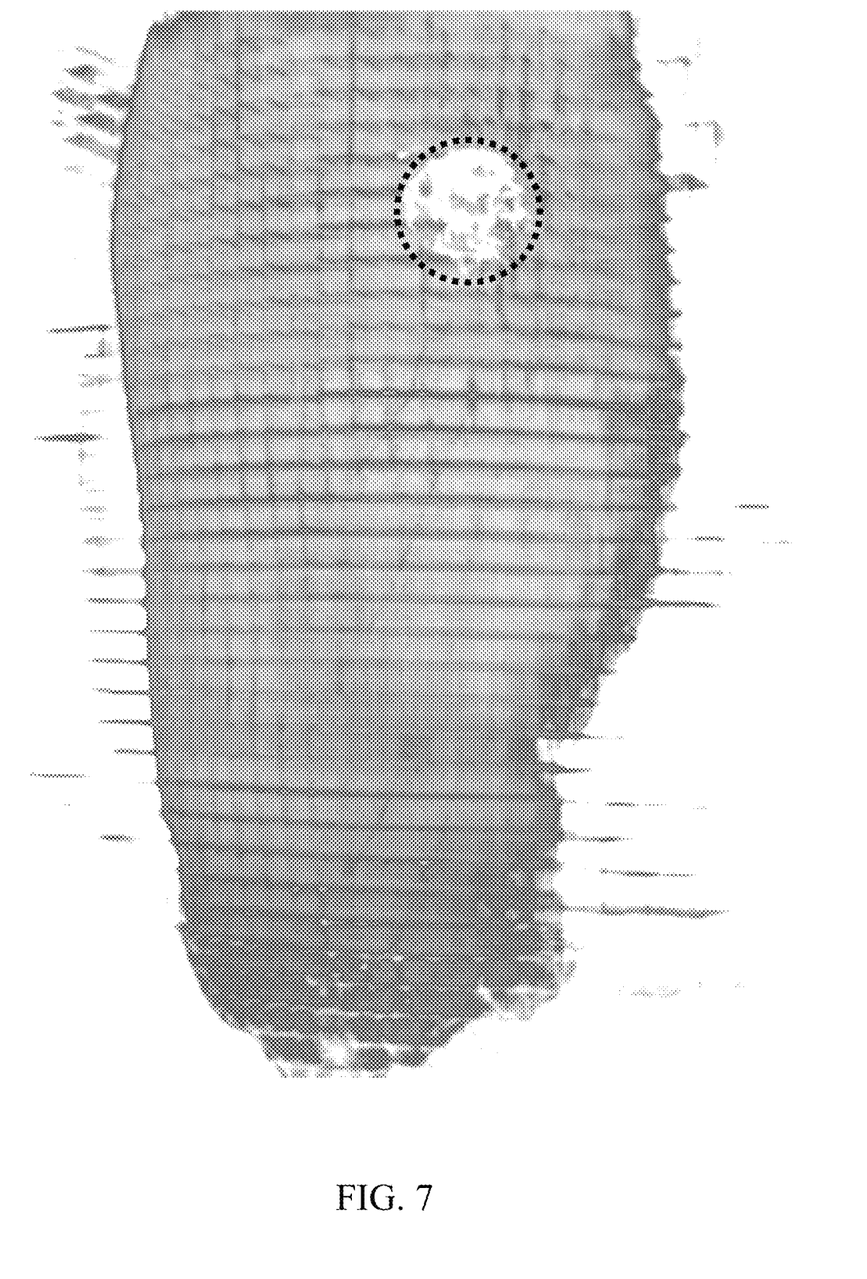
FIG. 7 shows a screenshot of an exemplary interface for viewing medical image data with a heatmap identification of target anomalies.
Figure 8:
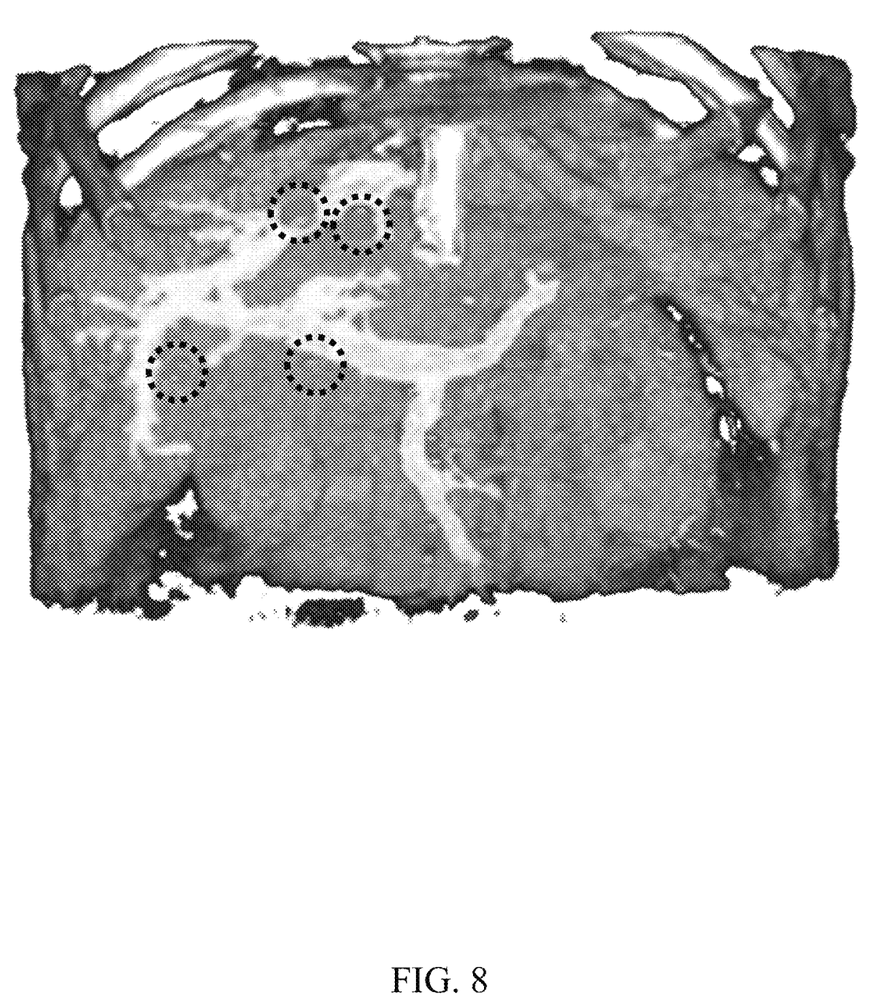
FIG. 8 shows a screenshot of another exemplary interface for viewing medical image data with a heatmap identification of target anomalies.

The heatmap output may include pre-rendered graphics or models, or may include metadata that is usable to overlay or insert visual indicators onto a rendered image. FIGS. 7 and 8 each provide examples of 3D models with identified target tissues being marked. FIG. 7 also visually illustrates the chunks that the image is divided into, while other rendered heatmaps, such as that of FIG. 8, may illustrate the individual chunks. The system may then analyze (422) the heatmap output to produce a set of accuracy metrics (424), and may provide the completed results (426) to the user.

In accordance with the present disclosure, labeled mammalian data of one or more species is utilized during AI network model training to detect abnormalities in mammalian species. In some embodiments, machine learning network training is performed using exclusively labeled human data. In other embodiments, machine learning network training is performed using a combination of labeled human data and labeled animal data (i.e., non-human). In accordance with various embodiments, when the network is tested, labeled animal data is used to ensure that the reported accuracy of the network is focused on how well it generalizes to the targeted problem space of the animal. In any event, the presently disclosed systems and methods can leverage the similarities in labeled mammalian data to help compensate for the lack of data needed to properly learn to select and differentiate abstract features, which allows for a generalized network model solution.

Methodologies in accordance with the presently disclosure beneficially allow for the rapid development of machine learning solutions including but not limited to for human radiology, among other imaging modalities, using learning developed from animal-based datasets or other high quality dataset sources. As such, the systems and methods described herein can be utilized across a variety of disciplines, including, but not limited to, general practices, radiologists, internal medicine specialists, diagnosticians, and imaging specialists, which are generally referred to herein as "medical professionals."

Once the network has been trained using the process outlined in the preceding sections, the network trained using transfer learning can be applied on live data in the field. In one embodiment, data will be received in the form of a 2-D or 3-D scan. The data for this embodiment will be separated into chunks comprising portions of the scan and then fed through the network. The network will output confidence values for each voxel, which are reconstructed into a heatmap matching the pattern of the original scan. This heatmap will be refined by the use of intervals to select the whole or a portion that will be designated as the identified anomaly. This portion of the heatmap will then be overlaid on the original scan to provide an assessment of where the medical issue is.

In accordance with various embodiments, the systems and methods can be used to help optimize a model when also provided with suitable preprocessing, sampling methods, settings, and data sets. As one example, this could include a cloud platform or local software application that analyzes past case studies to form reference points for anomalous findings and can report on those finds, no matter how small. Thus, a more diagnostically complete visual analysis of the case can be provided without limiting the ultimate findings to particular diseases that visually present within predefined, specific parameters.

In general, it will be apparent to one of ordinary skill in the art that at least some of the embodiments described herein can be implemented in many different embodiments of software, firmware, and/or hardware. The software and firmware code can be executed by a processor or any other similar computing device. The software code or specialized control hardware that can be used to implement embodiments is not limiting. For example, embodiments described herein can be implemented in computer software using any suitable computer software language type, using, for example, conventional or object-oriented techniques. Such software can be stored on any type of suitable computer-readable medium or media, such as, for example, a magnetic or optical storage medium. The operation and behavior of the embodiments can be described without specific reference to specific software code or specialized hardware components. The absence of such specific references is feasible, because it is clearly understood that artisans of ordinary skill would be able to design software and control hardware to implement the embodiments based on the present description with no more than reasonable effort and without undue experimentation.

Moreover, the processes described herein can be executed by programmable equipment, such as computers or computer systems and/or processors. Software that can cause programmable equipment to execute processes can be stored in any storage device, such as, for example, a computer system (nonvolatile) memory, an optical disk, magnetic tape, or magnetic disk. Furthermore, at least some of the processes can be programmed when the computer system is manufactured or stored on various types of computer-readable media.

It can also be appreciated that certain portions of the processes described herein can be performed using instructions stored on a computer-readable medium or media that direct a computer system to perform the process steps. A computer-readable medium can include, for example, memory devices such as diskettes, compact discs (CDs), digital versatile discs (DVDs), optical disk drives, or hard disk drives. A computer-readable medium can also include memory storage that is physical, virtual, permanent, temporary, semi-permanent, and/or semi-temporary.

A "computer," "computer system," "host," "server," or "processor" can be, for example and without limitation, a processor, microcomputer, minicomputer, server, mainframe, laptop, personal data assistant (PDA), wireless e-mail device, cellular phone, pager, processor, fax machine, scanner, or any other programmable device configured to transmit and/or receive data over a network. Computer systems and computer-based devices disclosed herein can include memory for storing certain software modules used in obtaining, processing, and communicating information. It can be appreciated that such memory can be internal or external with respect to operation of the disclosed embodiments.

The machine learning code can access the memory locations that have been set forth by the CPU or GPU to iterate through the network architecture and decode and execute the instructions which have been stored in memory. These sessions are computationally expensive and can be executed using GPUs and CPUs. The CPU or GPU, instructed by the iterator, can create a location to store the data either in entirety, in part, a variation of the data or location/orientational linking data. The data can be stored into memory which can include but not limited to RAM or external storage devices. The instructions dictate how the network will operate and function. Once the GPU has access to the instructions in memory, it then uses the instructions to assemble and run the data though the Neural Network, which is computed on the distributed cores of the GPU.

The Neural Network is constructed out of weights, biases, and a set of rules that describe the effect that these weights have on the input data as it is fed through a set of intermediate memory states. These portions may be randomized, pre-set, or loaded from an existing checkpoint. The training algorithm, which is stored in RAM or secondary allocated memory location and executed using either or both of the CPU and GPU in various embodiments, uses the results from the GPU's computation of the neural network to modify the weights and biases such that the network constructed from the modified weights and biases is mathematically optimized to perform more accurately on the data than the previous iteration of the network was capable of achieving. This process is repeated with different chunks, batches, and methods in varying embodiments in such a manner that allows for the creation of networks able to accurately perform the requisite tasks (i.e. identifying anomalies in the reconstructed medical scans).

The networks are evaluated on the GPU using a similar process to the training in that the data loaded in memory is used by the GPU to complete the calculation of a neural network. The results of these evaluations are stored and used to determine the accuracy or behavior of the network, which can be further specified and elaborated on in the context of the algorithm. The description of such settings which control the process of how the network is trained, evaluated, and tested are referred to as hyperparameters and are generally designated by the user in some embodiments and by automated algorithms in other embodiments. The weights and biases that constitute the network may be stored to a data file for later reconstruction (including but not limited to the .hdf5 format or more broadly any other file format that contains matrices of numbers in an ordered fashion). The resulting data file or any other data file of similar purpose can also be re-read and used to construct a neural network that behaves in identical fashion to that network which was used to generate the file.

In various embodiments disclosed herein, a single component can be replaced by multiple components and multiple components can be replaced by a single component to perform a given function or functions. Except where such substitution would not be operative, such substitution is within the intended scope of the embodiments. The computer systems can comprise one or more processors in communication with memory (e.g., RAM or ROM) via one or more data buses. The data buses can carry electrical signals between the processor(s) and the memory. The processor and the memory can comprise electrical circuits that conduct electrical current. Charge states of various components of the circuits, such as solid state transistors of the processor(s) and/or memory circuit(s), can change during operation of the circuits.

Some of the figures can include a flow diagram. Although such figures can include a particular logic flow, it can be appreciated that the logic flow merely provides an exemplary implementation of the general functionality. Further, the logic flow does not necessarily have to be executed in the order presented unless otherwise indicated. In addition, the logic flow can be implemented by a hardware element, a software element executed by a computer, a firmware element embedded in hardware, or any combination thereof.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art. Rather it is hereby intended the scope of the invention to be defined by the claims appended hereto.

Applications for the technology within the realm of cardiology may include but are not limited to; Vertebral Heart Score, Cardiomegaly, Arrhythmia, Coronary Artery Blockages, Aortic Occlusions, Cardiac Blockages, Aorta disease and Marfan syndrome, Congenital heart disease, Coronary artery disease, Deep Vein Thrombosis, Pulmonary Embolism, Mitral Regurgitation, Mitral Valve Dysplasia, Tricuspid Valve Dysplasia, Mitral Valve Stenosis, Aortic Stenosis, Patent Ductus Arteriosus, Ventricular Septal Defects, Atrial Septal Defects, Dilated Cardiomyopathy, Arrhythmic Cardiomyopathy, Heartworm Disease, Pulmonic Stenosis, and Tetralogy of Fallot.

Applications for the technology within the realm of gastrointestinal may include but are not limited to; Esophageal Distention, Barrett's Esophagus, Esophageal Foreign Body, Pleural Gas, Pleural Fluid, Cranioventral Parenchymal Pattern, Caudodorsal Parenchymal Pattern, Nodular or Miliary Pattern, Pulmonary Nodule(s), Gastric Distention, Gastric Foreign Material, Gastric Dilatation and Volvulus Small Intestinal Foreign Material Small Intestinal Plication, Two Populations of Small Intestine Colonic Foreign Material.

Applications for the technology within the realm of abdominal or renal regions may include but are not limited to; Hepatomegaly, Mid Abdominal Mass, Splenomegaly, Peritoneal Fluid, Retroperitoneal Fluid, Retroperitoneal Lymphadenopath, Renal Mineralization, Renomegaly, Small Kidney, Urinary Bladder Calculi, Urethral Calculi, Prostatomegaly, Prostatic Mineralization.

Applications for the technology within the realm of skeletal and thoracic regions may include but are not limited to; Cervical Disc Space Narrowing Spondylosis, Thoracolumbar Disk Space Narrowing, Interstitial Pattern, Bronchointerstitial Pattern, Bronchial Pattern, Pulmonary Mass (es), Appendicular Fracture, Aggressive Bone Lesion.

Applications for the technology within the realm of radiology may include but are not limited to; Lung Cancer, Colon Cancer, Colorectal Cancer, Cervical Cancer, Gastric Cancer, Bladder Cancer, Liver Cancer, Hepatic Vessel Cancer, Adrenal Gland Cancer, Renal Cancer, Pancreatic Cancer, Thyroid Cancer, Mammary Cancer, Ovarian Cancer, Prostate Cancer, Squamous Cell Carcinoma, Basal Cell Carcinoma, Melanoma, Melanocytic Nevus, Actinic Keratosis, Benign Keratosis, Dermatofibroma, Vascular Lesions, Oesophageal Adenocarcinoma, Neuro-Blastoma, OsteoArthritis, Rib Fractures, Structural Nerve Damage, Scoliosis, Vertebral Fracture, Herniated Disc, Pneumonia, Pneumothorax, Lung Ventilation, Covid-19.

Applications for the technology within the realm of neurology may include but are not limited to; Mild Cognitive Impairment, Traumatic Brain Injury, Concussions, Alzheimer's Disease, Dementia, Parkinson's Disease, Stroke Lesions, Multiple Sclerosis, Brain Tumors, Intracranial Hemorrhage, Degenerative Lumbosacral Stenosis, Degenerative Myelopathy, Diffuse Idiopathic Skeletal Hyperostosis, Intervetrebal Disk Disease.

Applications for the technology within the realm of histopathology may include but are not limited to; Tumor Proliferation, Nuclear Atypia Score, Signet Ring Cell Detection, Multiple Myloma, Abnormality, Segmentation, Lymphocytes, Macrophages, Neutrophils, Epithelials, Mitochondrial Segmentation, Normal vs Bening vs Malignant White Cell Cancer Analysis, Metastasis Tissue, Immune Mediated, Hemolytic Anemia, immune mediated thrombocytopenia, Anaplastic Anemia, Antibody-Dependent, Cellular Cytotoxicity, Adenocarcinoma, Atypical Glandular Cells, and Lymphoma.

Applications for the technology within the realm of ophthalmology may include but are not limited to; Ocular Disease, Optical Hemorrhage, Optical Anuerisms & Microanuerisms, Hard Exudates, Soft Exudates, Retinal Fundus Disease, Diabetic Retinopathy, Blindness, Macular Degeneration, Glaucoma, Optic Disc Displacement, Cataracts, Subconjunctival hemorrhage, Ambylopia, Strabismus, Conjunctivitis, and Keratoconus.

Applications for the technology within the realm of cardiology may include but are not limited to; Vertebral Heart Score, Cardiomegaly, Arrhythmia, Coronary Artery Blockages, Aortic Occlusions, Cardiac Blockages, Aorta disease and Marfan syndrome, Congenital heart disease, Coronary artery disease, Deep Vein Thrombosis, Pulmonary Embolism, Mitral Regurgitation, Mitral Valve Dysplasia, Tricuspid Valve Dysplasia, Mitral Valve Stenosis, Aortic Stenosis, Patent Ductus Arteriosus, Ventricular Septal Defects, Atrial Septal Defects, Dilated Cardiomyopathy, Arrhythmic Cardiomyopathy, Heartworm Disease, Pulmonic Stenosis, and Tetralogy of Fallot.

Applications for the technology within the realm of gastrointestinal may include but are not limited to; Esophageal Distention, Barrett's Esophagus, Esophageal Foreign Body, Pleural Gas, Pleural Fluid, Cranioventral Parenchymal Pattern, Caudodorsal Parenchymal Pattern, Nodular or Miliary Pattern, Pulmonary Nodule(s), Gastric Distention, Gastric Foreign Material, Gastric Dilatation and Volvulus Small Intestinal Foreign Material Small Intestinal Plication, Two Populations of Small Intestine Colonic Foreign Material.

Applications for the technology within the realm of abdominal or renal regions may include but are not limited to; Hepatomegaly, Mid Abdominal Mass, Splenomegaly, Peritoneal Fluid, Retroperitoneal Fluid, Retroperitoneal Lymphadenopath, Renal Mineralization, Renomegaly, Small Kidney, Urinary Bladder Calculi, Urethral Calculi, Prostatomegaly, Prostatic Mineralization.

Applications for the technology within the realm of skeletal and thoracic regions may include but are not limited to; Cervical Disc Space Narrowing Spondylosis, Thoracolumbar Disk Space Narrowing, Interstitial Pattern, Bronchointerstitial Pattern, Bronchial Pattern, Pulmonary Mass(es), Appendicular Fracture, Aggressive Bone Lesion.

Applications for the technology within the realm of radiology may include but are not limited to; Lung Cancer, Colon Cancer, Colorectal Cancer, Cervical Cancer, Gastric Cancer, Bladder Cancer, Liver Cancer, Hepatic Vessel Cancer, Adrenal Gland Cancer, Renal Cancer, Pancreatic Cancer, Thyroid Cancer, Mammary Cancer, Ovarian Cancer, Prostate Cancer, Squamous Cell Carcinoma, Basal Cell Carcinoma, Melanoma, Melanocytic Nevus, Actinic Keratosis, Benign Keratosis, Dermatofibroma, Vascular Lesions, Oesophageal Adenocarcinoma, Neuro-Blastoma, OsteoArthritis, Rib Fractures, Structural Nerve Damage, Scoliosis, Vertebral Fracture, Herniated Disc, Pneumonia, Pneumothorax, Lung Ventilation, Covid-19.

Applications for the technology within the realm of neurology may include but are not limited to; Mild Cognitive Impairment, Traumatic Brain Injury, Concussions, Alzheimer's Disease, Dementia, Parkinson's Disease, Stroke Lesions, Multiple Sclerosis, Brain Tumors, Intracranial Hemorrhage, Degenerative Lumbosacral Stenosis, Degenerative Myelopathy, Diffuse Idiopathic Skeletal Hyperostosis, Intervetrebal Disk Disease.

Applications for the technology within the realm of histopathology may include but are not limited to; Tumor Proliferation, Nuclear Atypia Score, Signet Ring Cell Detection, Multiple Myloma, Abnormality, Segmentation, Lymphocytes, Macrophages, Neutrophils, Epithelials, Mitochondrial Segmentation, Normal vs Bening vs Malignant White Cell Cancer Analysis, Metastasis Tissue, Immune Mediated, Hemolytic Anemia, immune mediated thrombocytopenia, Anaplastic Anemia, Antibody-Dependent, Cellular Cytotoxicity, Adenocarcinoma, Atypical Glandular Cells, Lymphoma.

Applications for the technology within the realm of ophthalmology may include but are not limited to; Ocular Disease, Optical Hemorrhage, Optical Anuerisms & Microanuerisms, Hard Exudates, Soft Exudates, Retinal Fundus Disease, Diabetic Retinopathy, Blindness, Macular Degeneration, Glaucoma, Optic Disc Displacement, Cataracts, Subconjunctival hemorrhage, Ambylopia, Strabismus, Conjunctivitis, Keratoconus.

The invention claimed is:

1. A method for training a neural network for medical image analysis using mammalian transfer learning, the method comprising:
   (a) receiving, by a processor, one or more comparative datasets, wherein each of the one or more comparative datasets comprises labeled image data associated with a species;
   (b) creating, by the processor, a mixed domain dataset based on the one or more comparative datasets;
   (c) for each image of a plurality of images of the mixed domain dataset:
      (i) defining, by the processor, a plurality of chunks within that image, wherein the size of each of the plurality of chunks is selected to obfuscate a species of the source of the image;
      (ii) adding, by the processor, the plurality of chunks of that image and any associated labels to a mixed domain training dataset;
   (d) by the processor, and with the neural network:
      (i) training the neural network to identify a medical characteristic of a case study from a target species based on the mixed domain training set and the associated labels, wherein the one or more species of the one or more comparative datasets includes at least one species other than the target species; and
      (ii) validating the trained neural network based upon a validation dataset selected from the mixed domain dataset; and
   (e) creating, by the processor, a checkpoint based on the trained and validated neural network.

2. The method of claim 1, wherein the associated labels comprise one of:
   (a) a set of per-pixel characteristics that describe pixels of the chunk; or
   (b) a set of per-voxel characteristics that describe voxels of the chunk.

3. The method of claim 1, wherein the one or more comparative datasets includes a first comparative dataset associated with the target species, and a second comparative dataset associated with a species other than the target species.

4. The method of claim 1, wherein the plurality of images includes one or more of two-dimensional images, three-dimensional images, and four-dimensional images.

5. The method of claim 1, wherein the processor comprises one or more of:
   (a) one or more central processing units in communication with each other directly or over a network; and
   (b) one or more graphic processing units in communication with each other directly or over a network.

6. The method of claim 1, further comprising:
   (a) receiving, by the processor, the case study from a user device, the case study comprising a set of medical images associated with a patient;
   (b) defining, by the processor, a second plurality of chunks within the set of medical images, wherein the size of each of the second plurality of chunks is selected to obfuscate a species of the patient;
   (c) analyzing, by the processor, and with the checkpoint, the second plurality of portions to identify the medical characteristic within the set of medical images; and
   (d) providing, by the processor, an indication of the medical characteristic within the set of medical images.

7. The method of claim 6, wherein providing the indication of the medical characteristic comprises:
   (a) causing, by the processor, at least one medical image of the set of medical images to display on the user device; and
   (b) causing, by the processor, a heatmap comprising the indication of the medical characteristic to be displayed with at least one medical image.

8. The method of claim 1, wherein:
   (a) each of the one or more comparative datasets comprises labeled image data associated with a species and one or more problem classes, wherein the one or more problem classes describes one or more medical anomalies; and
   (b) the one or more problem classes of the one or more comparative datasets includes at least one problem class that does not describe the medical characteristic.

9. The method of claim 1, further comprising testing the checkpoint based upon a testing dataset selected from the mixed domain dataset, wherein the testing dataset and the validation dataset are each associated with the target species.

10. The method of claim 1, further comprising training the neural network to identify the medical characteristic in less than about 100 epochs.

11. The method of claim 1, wherein the one or more comparative datasets comprises a first comparative dataset associated with a human, and the target species is any within the class of Mammalia other than human.

12. The method of claim 1, wherein the one or more comparative datasets comprises between about 10 and about 20 comparative datasets.

13. A system comprising a neural network configured for medical image analysis and trained using mammalian transfer learning, the system comprising a processor configured to:
   (a) receive one or more comparative datasets, wherein each of the one or more comparative datasets comprises labeled image data associated with a species;
   (b) create a mixed domain dataset based on the one or more comparative datasets;
   (c) for each image of a plurality of images of the mixed domain dataset:
      (i) define a plurality of chunks within that image, wherein the size of each of the plurality of chunks is selected to obfuscate a species of the source of the image;
      (ii) add the plurality of chunks of that image and any associated labels to a mixed domain training dataset;
   (d) with the neural network:
      (i) train the neural network to identify a medical characteristic of a case study from a target species based on the mixed domain training set and the associated labels, wherein the one or more species of the one or more comparative datasets includes at least one species other than the target species; and
      (ii) validate the trained neural network based upon a validation dataset selected from the mixed domain dataset; and (e) create a checkpoint based on the trained and validated neural network.

14. The system of claim 13, wherein the processor comprises one or more of:
   (a) one or more central processing units in communication with each other directly or over a network; and
   (b) one or more graphic processing units in communication with each other directly or over a network.

15. The system of claim 13, wherein the processor is further configured to:
   (a) receive the case study from a user device, the case study comprising a set of medical images associated with a patient;
   (b) define a second plurality of chunks within the set of medical images, wherein the size of each of the second plurality of chunks is selected to obfuscate a species of the patient;
   (c) analyze, with the checkpoint, the second plurality of portions to identify the medical characteristic within the set of medical images; and
   (d) provide an indication of the medical characteristic within the set of medical images.

16. The system of claim 15, wherein the processor is further configured to, when providing the indication of the medical characteristic:
   (a) cause at least one medical image of the set of medical images to display on the user device; and
   (b) cause a heatmap comprising the indication of the medical characteristic to be displayed with at least one medical image.

17. The system of claim 13, wherein:
   (a) each of the one or more comparative datasets comprises labeled image data associated with a species and one or more problem classes, wherein the one or more problem classes describes one or more medical anomalies; and
   (b) the one or more problem classes of the one or more comparative datasets includes at least one problem class that does not describe the medical characteristic.

18. The system of claim 13, wherein the processor is further configured to test the checkpoint based upon a testing dataset selected from the mixed domain dataset, wherein the testing dataset and the validation dataset are each associated with the target species.

19. The system of claim 13, wherein:
   (a) the one or more comparative datasets comprises a first comparative dataset associated with a human, and the target species is any within the class of Mammalia other than human; and
   (b) the one or more comparative datasets comprises between about 10 and about 20 comparative datasets.

* * * * *